(12) United States Patent
Zhou (10) Patent No.: US 12,089,813 B1
(45) Date of Patent: Sep. 17, 2024

(54) DISPOSABLE SECTION OF ENDOSCOPE HANDLE, ENDOSCOPE HANDLE, AND ENDOSCOPE

(71) Applicant: HUNAN VATHIN MEDICAL INSTRUMENT CO. LTD, Xiangtan (CN)

(72) Inventor: Zhenhua Zhou, Xiamen (CN)

(73) Assignee: HUNAN VATHIN MEDICAL INSTRUMENT CO. LTD, Xiangtan (CN)

( * ) Notice: Subject to any disclaimer, the term of this patent is extended or adjusted under 35 U.S.C. 154(b) by 0 days.

(21) Appl. No.: 18/695,363

(22) PCT Filed: Mar. 13, 2023

(86) PCT No.: PCT/CN2023/081133
§ 371 (c)(1),
(2) Date: Mar. 26, 2024

(87) PCT Pub. No.: WO2023/226536
PCT Pub. Date: Nov. 30, 2023

(30) Foreign Application Priority Data

May 25, 2022 (CN) .......................... 202210575884.8

(51) Int. Cl.
*A61B 1/00* (2006.01)
*A61B 1/005* (2006.01)
*A61M 25/01* (2006.01)

(52) U.S. Cl.
CPC ...... *A61B 1/00105* (2013.01); *A61B 1/00103* (2013.01); *A61B 1/00128* (2013.01);
(Continued)

(58) Field of Classification Search
CPC ............ A61B 1/00105; A61B 1/00103; A61B 1/00128; A61B 1/0052; A61B 1/0057;
(Continued)

(56) References Cited

U.S. PATENT DOCUMENTS 8,177,710 B1 * 5/2012 Hosaka .................... A61B 1/05
600/146
2006/0069311 A1 * 3/2006 Sullivan ............... A61B 1/0055
600/152

(Continued)

FOREIGN PATENT DOCUMENTS

CN 105517480 A 4/2016
CN 109480749 A 3/2019
(Continued)

*Primary Examiner* — Timothy J Neal
*Assistant Examiner* — James Edward Boice
(74) *Attorney, Agent, or Firm* — Bayramoglu Law Offices LLC (57) ABSTRACT

A disposable section of an endoscope handle, an endoscope handle, and an endoscope are provided, including a housing which includes a proximal end provided with a connecting portion, where the connecting portion is configured to be detachably connected to a reusable section of the handle; and a first transmission assembly including a first traction wire, a second traction wire, and a first connecting portion, where a proximal end surface of the housing forms a first curved movement path; the first curved movement path is orthogonal to an axial direction of the proximal end surface and located at a periphery of the proximal end surface of the housing; and the first connecting portion is movable along the first curved movement path.

17 Claims, 6 Drawing Sheets

(52) U.S. Cl.
CPC .......... *A61B 1/0052* (2013.01); *A61B 1/0057* (2013.01); *A61M 25/0136* (2013.01); *A61M 25/0147* (2013.01)

(58) Field of Classification Search
CPC ...... A61B 2017/0046; A61M 25/0136; A61M 25/0147
USPC .................................................. 600/131, 197
See application file for complete search history.

(56) References Cited

U.S. PATENT DOCUMENTS

| | | | |
|---|---|---|---|
| 2014/0251042 A1* | 9/2014 | Asselin | F16H 21/40 74/89 |
| 2017/0086651 A1* | 3/2017 | Sato | G02B 23/2476 |
| 2017/0268639 A1 | 9/2017 | Asselin et al. | |

FOREIGN PATENT DOCUMENTS

| | | |
|---|---|---|
| CN | 114190866 A | 3/2022 |
| CN | 216256998 U | 4/2022 |
| CN | 114795069 A | 7/2022 |
| JP | H07178041 A | 7/1995 |
| JP | 2005218569 A | 8/2005 |
| JP | 2017176697 A | 10/2017 |
| WO | 2022001994 A1 | 1/2022 |
| WO | 2022062513 A1 | 3/2022 |

\* cited by examiner

DISPOSABLE SECTION OF ENDOSCOPE HANDLE, ENDOSCOPE HANDLE, AND ENDOSCOPE

CROSS-REFERENCE TO THE RELATED APPLICATIONS

This application is the national phase entry of International Application No. PCT/CN2023/081133, filed on Mar. 13, 2023, which is based upon and claims priority to Chinese Patent Application No. 202210575884.8, filed on May 25, 2022, the entire contents of which are incorporated herein by reference.

TECHNICAL FIELD

The present disclosure belongs to the technical field of endoscopy, and relates to a disposable section of an endoscope handle, an endoscope handle, and an endoscope.

BACKGROUND

An inserting unit, with at least lighting and shooting functions, of an endoscope enters the human body through a natural orifice or a surgical incision to detect the human body's cavity environment. The bending angle of an active bending section located at the front end of the inserting unit of the endoscope is adjusted by operating a handle located outside the human body such that the active bending section is deflected in a preset direction to provide a wider visual angle range for observation.

Typically, the inserting unit of the endoscope is provided with an instrument channel. During the detection or treatment of the human body's cavity environment, excess fluid of the internal tissue of the human body is extracted and guided to the outside of the human body through the instrument channel. In addition, through the instrument channel, external instruments such as biopsy forceps can be delivered into the body cavity to collect a part of the human tissue for biopsy detection after reaching a target tissue.

When the inserting unit is inserted into the human body, its external part and internal instrument channel are severely contaminated. Typically, after the use, the inserting unit and the handle are discarded as a whole, resulting in high costs, and patients are difficult to support the high cost of equipment. To address the cost issue, in the prior art, the handle is divided into a disposable part and a reusable part. However, the connecting process of the disposable part and the reusable part in the prior art is complex, increasing the operational difficulty for doctors. Meanwhile, the disposable part needs a new structural design and has a complex force transmission process, resulting in high fabrication costs.

SUMMARY

An objective of the present disclosure is to provide a disposable section of an endoscope handle, including:
- a housing, including a proximal end provided with a connecting portion, where the connecting portion configured to is configured to be detachably connected to a reusable section of the handle;
- an inserting unit, where a proximal end of the inserting unit is located at a distal end of the housing; and
- a first transmission assembly, including: a first traction wire, a second traction wire, and a first connecting portion, where the first traction wire and the second traction wire are located in the inserting unit of the endoscope; and a distal end of the first traction wire and a distal end of the second traction wire are connected to an active bending section at a distal end of the inserting unit, and a proximal end of the first traction wire and a proximal end of the second traction wire are connected to the first connecting portion, where
- a proximal end surface of the housing forms a first curved movement path; the first curved movement path is orthogonal to an axial direction of the proximal end surface and located at a periphery of the proximal end surface of the housing; and the first connecting portion is movable along the first curved movement path.

Preferably, the proximal end surface of the housing is provided with an annular groove; a rotating wheel is rotatably mounted at a central area of the annular groove; a curved guide groove is formed between an outer edge of the rotating wheel and a ring wall of the annular groove; and the first connecting portion is slidably provided in the curved guide groove.

Preferably, an outer ring wall surface of the rotating wheel is provided with an accommodating groove.

Preferably, two ends of the curved guide groove are respectively provided with a first through hole and a second through hole along the axial direction of the proximal end surface of the housing; and the first traction wire and the second traction wire are respectively threaded through the first through hole and the second through hole.

Preferably, a wheel disc is rotatably mounted at the proximal end surface of the housing; a first guide hole and a second guide hole are provided in the axial direction of the proximal end surface of the housing; the first guide hole and the second guide hole are located in the proximity of an outer ring wall of the wheel disc; an outer ring wall between the first guide hole and the second guide hole forms the first curved movement path; and the first connecting portion is abutted against an outer circumferential wall of the wheel disc.

Preferably, the proximal end surface of the housing is provided with a first accommodating groove; the first connecting portion is located in the first accommodating groove; and the first accommodating groove is curved.

Preferably, the first connecting portion is provided with a roller, and the roller is abutted against a side wall of the first accommodating groove.

Preferably, the disposable section of an endoscope handle further includes:
- a second transmission assembly, including: a third traction wire, a fourth traction wire, and a second connecting portion, where the third traction wire and the fourth traction wire are located in the inserting unit of the endoscope; and a distal end of the third traction wire and a distal end of the fourth traction wire are connected to the active bending section at the distal end of the inserting unit, and a proximal end of the third traction wire and a proximal end of the fourth traction wire are connected to the second connecting portion;
- the first transmission assembly is opposite to the second transmission assembly; and
- the proximal end surface of the housing is further provided with a second curved movement path; the second connecting portion is located on the second curved movement path; and the second curved movement path is curved.

An endoscope handle includes the above-mentioned disposable section and reusable section, where the disposable section and the reusable section are detachably connected; and a distal end of the reusable section is provided with a matched portion that is configured to be connected to the first connecting portion; and one of the first connecting portion and the matched portion is a male connecting element, and the other of the first connecting portion and the matched portion is a female connecting element.

An endoscope includes the above-mentioned endoscope handle.

Beneficial Effects

1. Compared to a linear movement path, in the present disclosure, the first curved movement path can provide a longer movement path within the same planar area. Thus, the first connecting portion can drive the first traction wire and the second traction wire to move for a longer distance, providing a larger bending angle for an active bending section.

2. In the present disclosure, the rotating wheel is rotatably located on the proximal end surface of the housing. When the first connecting portion is forced to move along the outer edge of the rotating wheel and when the first traction wire and the second traction wire move relative to the rotating wheel, the friction between the first connecting portion and the rotating wheel and the friction between the first traction wire as well as the second traction wire and the rotating wheel drive the rotating wheel to rotate. During the rotation process, the friction is reduced, which reduces the difficulty of operation as well as wear and faults.

3. Compared to the prior art, in the present disclosure, the housing of the disposable section does not require a pulley block mechanism for guidance. In addition to the first traction wire and the second traction wire, the rotating wheel and the first connecting portion are located on the proximal end surface of the housing of the disposable section, not occupying the internal space of the housing. Therefore, the internal space of the housing of the disposable section can be further optimized, thereby reducing the volume of the housing. Alternatively, the size of the housing remains unchanged, while the arrangement of wires or flexible circuit boards (FPCs) and instrument tubes for a camera module is eased. Therefore, compared to the prior art, in the present disclosure, the disposable section saves a large number of components, such as the pulley block mechanism, thereby reducing production costs and achieving a fast and convenient assembly process. During the assembly process, the first traction wire and the second traction wire are respectively threaded through the first through hole and the second through hole. The rotating wheel is provided on the mounting shaft, and the first connecting portion is provided at the outer edge of the rotating wheel and forms the curved guide groove together with the ring wall of the annular groove. The assembly process is simple and involves fewer parts, thereby improving production capacity and efficiency.

4. Compared to the prior art, the present disclosure only needs to connect one force transmission component, that is, the first connecting portion. The first connecting portion is connected to the first traction wire and the second traction wire to form a closed force driving circuit. When the first connecting portion is forced to move, it directly drives the first traction wire and the second traction wire to move synchronously, ensuring a good synchronous movement effect of the first traction wire and the second traction wire. When an operator connects the disposable section to the reusable section, the operator only needs to connect one force transmission component, that is, the first connecting portion, reducing the difficulty of connecting the disposable section and the reusable section. It should be noted that in the prior art, at least two force transmission components, typically two push rods, need to be connected. In addition, in the prior art, a signal connector for signal transmission, such as a Type-C connector needs to be connected. However, when there are many connecting positions between the disposable section and the reusable section, the connecting difficulty directly increases, and improper application of a force during operation can easily lead to damage to the Type-C connector. Due to the fact that the present disclosure only needs to connect one force transmission component, the connecting difficulty is reduced.

BRIEF DESCRIPTION OF THE DRAWINGS

To describe the technical solutions in the embodiments of the present disclosure more clearly, the following briefly introduces the drawings required for describing the embodiments or the prior art. Apparently, the drawings in the following description show merely some embodiments of the present disclosure, and persons of ordinary skill in the art may still derive other drawings from these drawings without creative efforts.

REFERENCE NUMERALS 10. disposable section; 11. inserting unit; 12. active bending section; 13. first connecting portion; 131. sliding portion; 132. connecting rod; 130. second connecting portion; 14. end cap; 141. curved guide groove; 101. annular groove; 1021. mounting hole; 102. rotating wheel; 1022. accommodating groove; 103. mounting shaft; 104. first through hole; 105. second through hole; 111. first traction wire; 112. second traction wire; 113. third traction wire; 114. fourth traction wire; 100. housing; 20. reusable section; 1000. curved guide groove; and 21. lever.

DETAILED DESCRIPTION OF THE EMBODIMENTS

The following description provides many different embodiments or examples for implementing different features of the present disclosure. The elements and arrangements described in the following specific examples are only intended to concisely express the present disclosure, and are only for illustration purposes, rather than to limit the present disclosure.

In order to make the objectives, technical solutions, and advantages of the embodiments of the present disclosure clearer, the technical solutions in the embodiments of the present disclosure will be clearly and completely described below in conjunction with the drawings in the embodiments of the present disclosure. Obviously, the described embodiments are some, rather than all of the embodiments of the present disclosure. On the basis of the embodiments of the present disclosure, all other embodiments obtained by a person of ordinary skill in the art without making creative efforts shall fall within the protection scope of the present disclosure. Therefore, the detailed description of the embodiments of the present disclosure in the drawings is not intended to limit the protection scope of the present disclosure, but merely represent the selected embodiments of the present disclosure. On the basis of the embodiments of the present disclosure, all other embodiments obtained by a person of ordinary skill in the art without making creative efforts shall fall within the protection scope of the present disclosure.

In the present disclosure, unless otherwise clearly specified, the terms "installation", "interconnection", "connection" and "fixation" etc. are intended to be understood in a broad sense. For example, the "connection" may be a fixed connection, removable connection or integral connection; may be a mechanical connection or electrical connection; may be a direct connection or indirect connection using a medium; and may be a communication or interaction between two elements. Those of ordinary skill in the art may understand specific meanings of the above terms in the present disclosure based on a specific situation. In addition, the terms such as "first", "second", and "third" are used only for the purpose of description and cannot be understood to indicate or imply relative importance.

In the present disclosure, unless otherwise expressly specified, when it is described that a first feature is "above" or "under" a second feature, it may indicate that the first feature is in direct contact with the second feature, or that the first feature and the second feature are not in direct contact with each other but are in contact via another feature between them. Moreover, "a first feature is above and on a second feature" includes "the first feature is directly above or obliquely above the second feature" or simply means that "the first feature is higher than the second feature". "A first feature is under and below a second feature" includes "the first feature is directly under or obliquely under the second feature" or simply means that "the first feature is lower than the second feature".

In addition, in the present disclosure, for the convenience of describing and understanding the positional relationship between components, "proximal end" and "distal end" refer to proximal and distal positions of a structure for in-vivo operation in an operating environment. For the same component, "proximal end" and "distal end" refer to the relative rather than absolute positional relationship of the component. Therefore, the understanding of "proximal end" and "distal end" should be based on the principles of the present disclosure, without deviating from the essence of the present disclosure.

Figure 1:
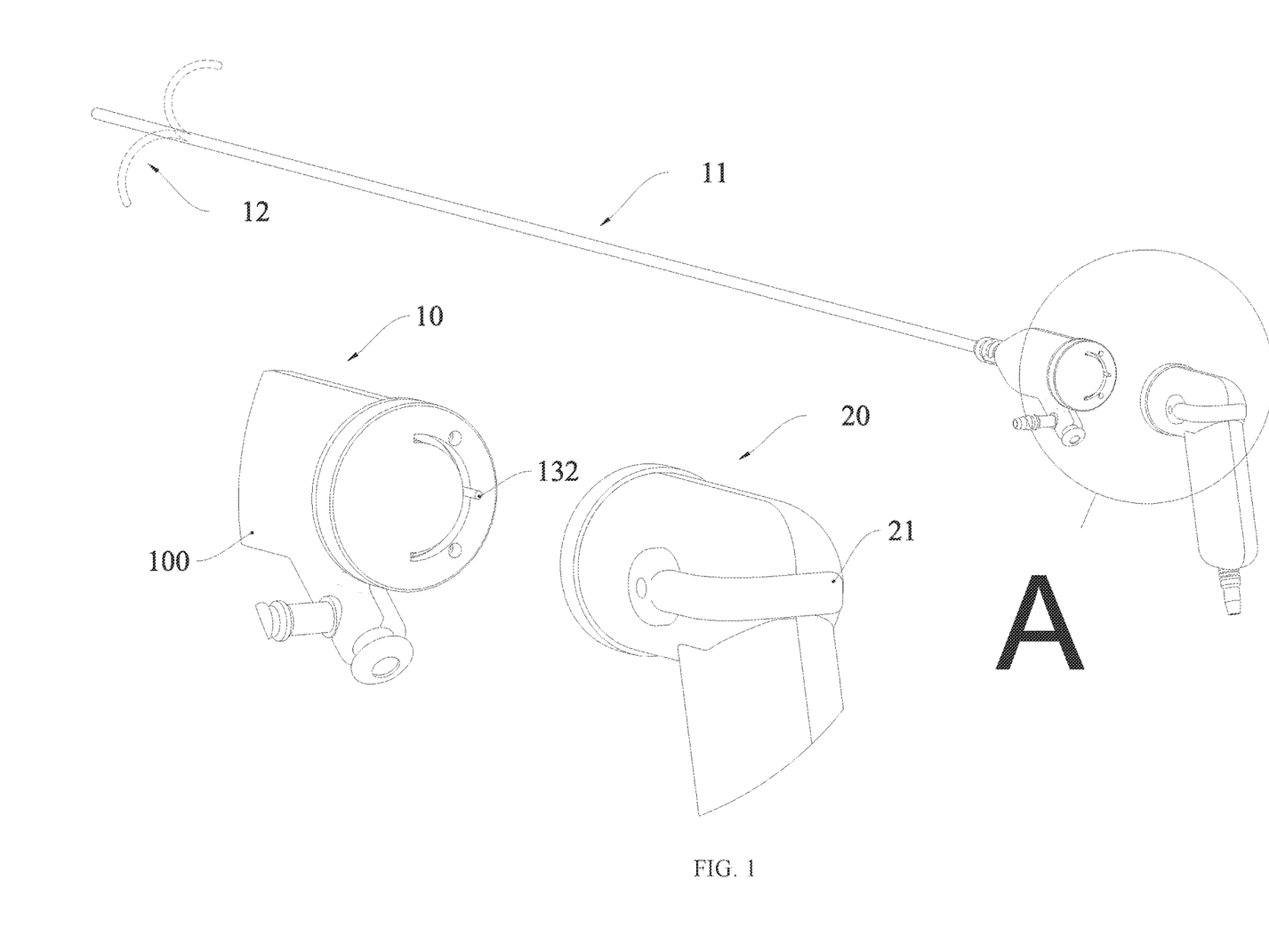
FIG. 1 is an exploded view of a disposable section and a reusable section according to the present disclosure.

As shown in FIG. 1, the present disclosure provides disposable section 10 of an endoscope handle.

The disposable section includes housing 100. The housing 100 includes a proximal end provided with a connecting portion. The connecting portion is configured to be detachably connected to reusable section 20 of the handle.

The disposable section includes inserting unit 11. A proximal end of the inserting unit 11 is located at a distal end of the housing 100. A distal end of the inserting unit 11 is provided with active bending section 12. The active bending section 12 includes snake bone units that are rotatable relatively to make the active bending section 12 bent.

The disposable section includes a first transmission assembly. The first transmission assembly includes: first traction wire 111, second traction wire 112, and first connecting portion 13. The first traction wire 111 and the second traction wire 112 are located in the inserting unit 11 of an endoscope. A distal end of the first traction wire 111 and a distal end of the second traction wire 112 are connected to the active bending section 12 at the distal end of the inserting unit 11. The first traction wire 111 and the second traction wire 112 are movable in opposite directions synchronously to move the active bending section 12 in a preset bending direction. A front end of the active bending section 12 is provided with a camera module. When the active bending section 12 bends in the preset direction, the camera module moves and a lens in the camera module captures image information of a target position. Further, to make the active bending section 12 rotate in the bending direction, a proximal end of the first traction wire 111 and a proximal end of the second traction wire 112 are connected to the first connecting portion 13. A proximal end surface of the housing 100 forms a first curved movement path. The first curved movement path is orthogonal to an axial direction of the proximal end surface and located at a periphery of the proximal end surface of the housing 100. The first connecting portion 13 is movable along the first curved movement path. It should be noted that compared to a linear movement path, the first curved movement path can provide a longer movement path within the same planar area. Specifically, when the proximal end surface of the housing 100 is quasi-circular, the first curved movement path can be formed on the periphery of the proximal end surface. In this way, the first connecting portion 13 can drive the first traction wire 111 and the second traction wire 112 to move for a longer distance, providing a larger bending angle for the active bending section 12. It should be noted that, compared to the prior art, the present disclosure only needs to connect one force transmission component, that is, the first connecting portion 13. The first connecting portion 13 is connected to the first traction wire 111 and the second traction wire 112 to form a closed force driving circuit. When the first connecting portion 13 is forced to move, it directly drives the first traction wire 111 and the second traction wire 112 to move synchronously, ensuring a good synchronous movement effect of the first traction wire 111 and the second traction wire 112. When an operator connects the disposable section 10 to the reusable section 20, the operator only needs to connect one force transmission component, that is, the first connecting portion 13, reducing the difficulty of connecting the disposable section 10 and the reusable section 20. It should be noted that in the prior art, at least two force transmission components, typically two push rods, need to be connected. In addition, in the prior art, a signal connector for signal transmission, such as a Type-C connector needs to be connected. However, when there are many connecting positions between the disposable section 10 and the reusable section 20, the connecting difficulty directly increases, and improper application of a force during operation can easily lead to damage to the Type-C connector. Due to the fact that the present disclosure only needs to connect one force transmission component, the connecting difficulty is reduced.

Figure 2:
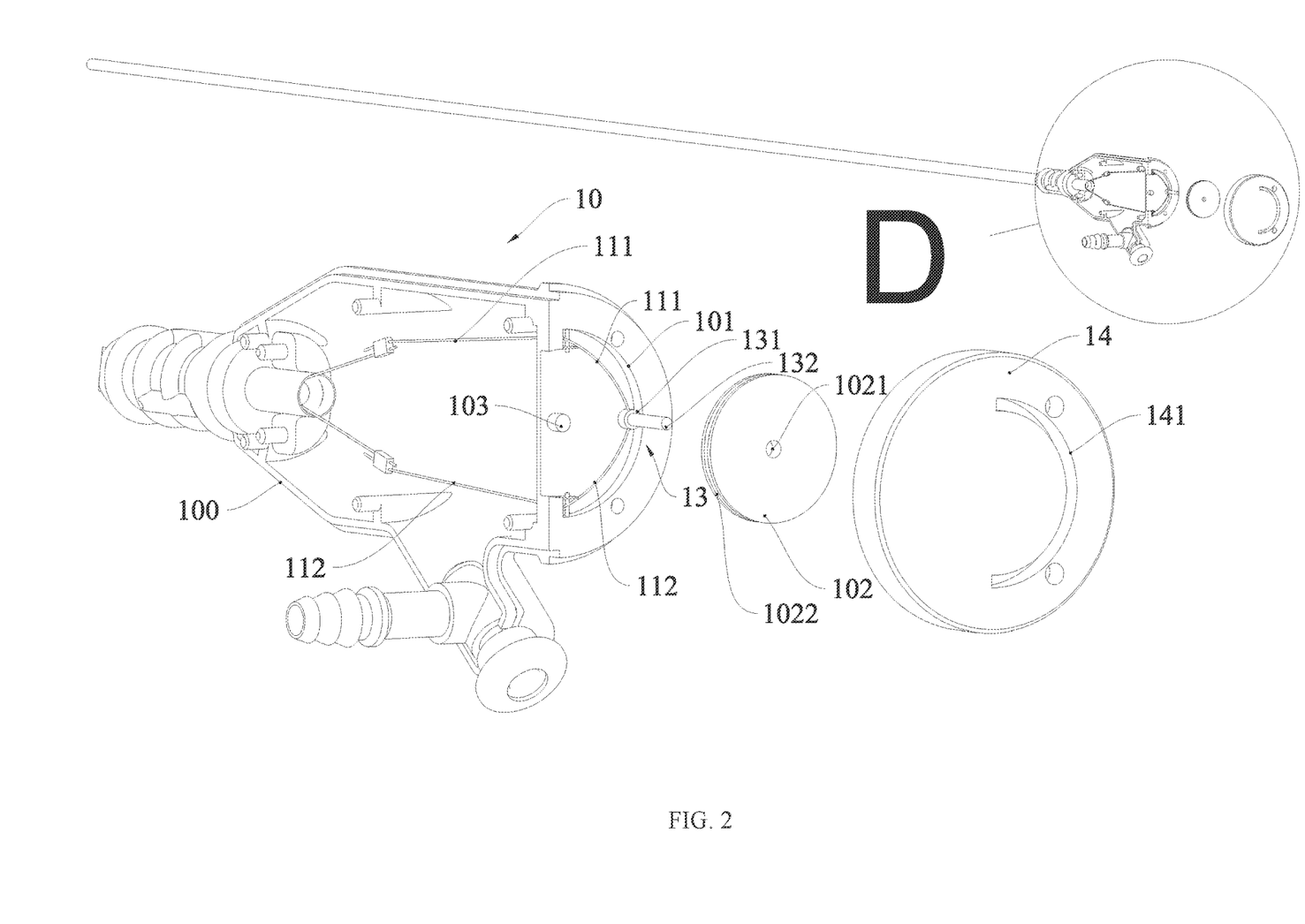
FIG. 2 is a first internal view of the disposable section according to the present disclosure.
Figure 3:
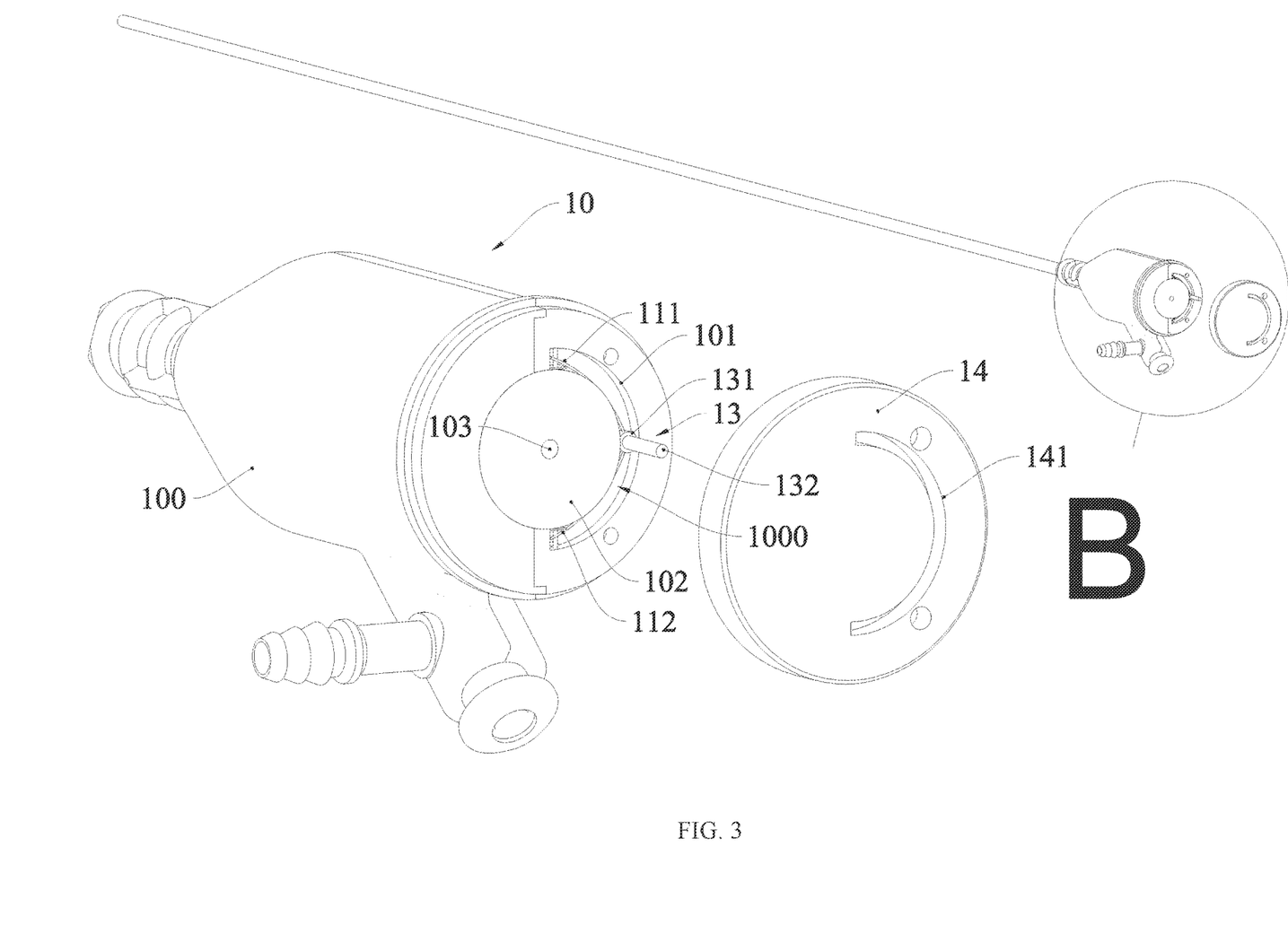
FIG. 3 is a second internal view of the disposable section according to the present disclosure.

As shown in FIGS. 2 and 3, in the embodiment of the present disclosure, preferably, the proximal end surface of the housing 100 is provided with annular groove 101. Rotating wheel 102 is rotatably mounted at a central area of the annular groove 101. Curved guide groove 141 is formed between an outer edge of the rotating wheel 102 and a ring wall of the annular groove 101. The first connecting portion 13 is slidably provided in the curved guide groove 141. It should be noted that in order to mount the rotating wheel 102, protruding mounting shaft 103 is provided in the central area of the annular groove 101. The mounting shaft 103 can be a cylindrical post that protrudes from the proximal end surface of the housing 100 and is integrated with the proximal end surface of the housing 100. Mounting hole 1021 of the rotating wheel 102 is sleeved on the post, and the rotating wheel 102 is rotatable around the post. To reduce a friction between the rotating wheel 102 and the post, lubricating oil can be applied before the rotating wheel and the post are mounted. Alternatively, the mounting shaft 103 is provided with a rotating disc. The rotating wheel 102 is provided on the rotating disc, effectively reducing the friction between the rotating wheel 102 and the mounting shaft 103. To prevent the rotating wheel 102 and the first connecting portion 13 from detaching along the axial direction of the proximal end surface of the housing 100, detachable end cap 14 is further provided on the proximal end surface of the housing 100. The end cap 14 is provided with curved accommodating groove 1022 that is adapted to the curved guide groove 141. A width of the curved accommodating groove 1022 is smaller than a width of the curved guide groove 141 to prevent the first connecting portion 13 from detaching from the curved accommodating groove 1022.

Preferably, in the above embodiment, it should be noted that the outer edge of the rotating wheel 102 directly defines the movement path of the first connecting portion 13 along the outer edge of the rotating wheel 102. Therefore, if the rotating wheel 102 is not rotatably fixed on the proximal end surface of the housing 100, when the first connecting portion 13 is forced to move, it will inevitably rub against the outer edge of the rotating wheel 102. Meanwhile, when the first traction wire 111 and the second traction wire 112 move, they will inevitably rub against an outer edge wall surface of the rotating wheel 102. As a result, a driving force for driving the first connecting portion 13 to move will increase. To solve this problem, as shown in FIGS. 2 and 3, the rotating wheel 102 is rotatably located on the proximal end surface of the housing 100. When the first connecting portion 13 is forced to move along the outer edge of the rotating wheel 102 and when the first traction wire 111 and the second traction wire 112 move relative to the rotating wheel 102, the friction between the first connecting portion 13 and the rotating wheel 102 and the friction between the first traction wire 111 as well as the second traction wire 112 and the rotating wheel drive the rotating wheel 102 to rotate. During the rotation process, the friction is reduced, which reduces the difficulty of operation as well as wear and faults.

To further improve the stability of the disposable section 10, preferably, an outer ring wall surface of the rotating wheel 102 is provided with the accommodating groove 1022. The first traction wire 111 and the second traction wire 112 are embedded in the accommodating groove 1022 to prevent the first connecting portion 13 from detaching along an axial direction of the rotating wheel 102 due to unstable force when the first connecting portion moves relative to the rotating wheel 102.

Figure 4:
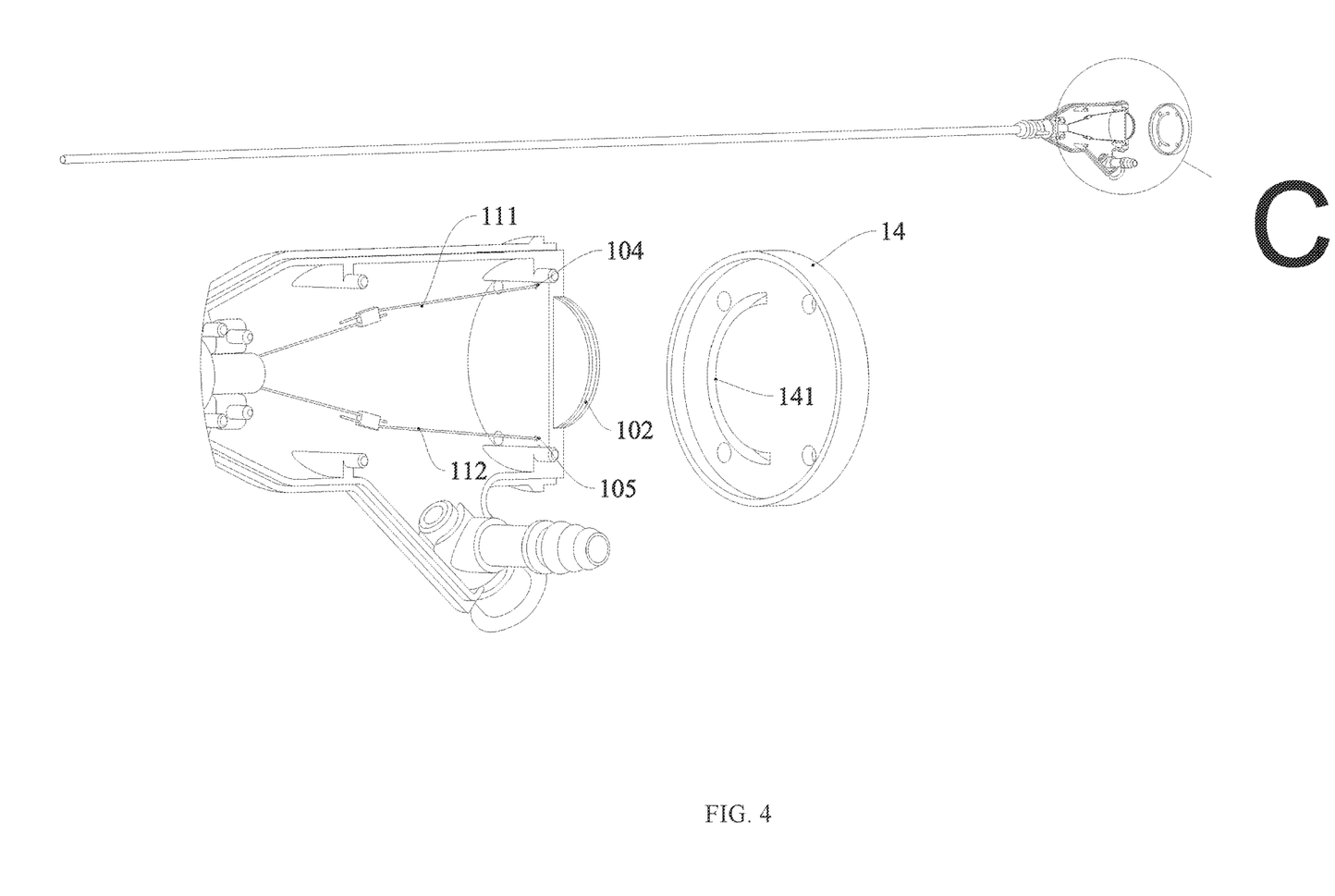
FIG. 4 is a third internal view of the disposable section according to the present disclosure.

As shown in FIG. 4, two ends of the curved guide groove 141 are respectively provided with first through hole 104 and second through hole 105 along the axial direction of the proximal end surface of the housing 100. The first traction wire 111 and the second traction wire 112 are respectively threaded through the first through hole 104 and the second through hole 105. The first through hole 104 and the second through hole 105 change a direction of force transmission for the first traction wire 111 and the second traction wire 112. Compared to the prior art, in the present disclosure, the housing 100 of the disposable section 10 does not require a pulley block mechanism for guidance. In addition to the first traction wire 111 and the second traction wire 112, the rotating wheel 102 and the first connecting portion 13 are located on the proximal end surface of the housing 100 of the disposable section 10, not occupying the internal space of the housing 100. Therefore, the internal space of the housing 100 of the disposable section 10 can be further optimized, thereby reducing the volume of the housing 100. Alternatively, the size of the housing 100 remains unchanged, while the arrangement of wires or flexible circuit boards (FPCs) and instrument tubes for a camera module is eased. Therefore, compared to the prior art, in the present disclosure, the disposable section 10 saves a large number of components, such as the pulley block mechanism, thereby reducing production costs and achieving a fast and convenient assembly process. During the assembly process, the first traction wire 111 and the second traction wire 112 are respectively threaded through the first through hole 104 and the second through hole 105. The rotating wheel 102 is provided on the mounting shaft 103, and the first connecting portion 13 is provided at the outer edge of the rotating wheel 102 and forms the curved guide groove 141 together with the ring wall of the annular groove 101. The assembly process is simple and involves fewer parts, thereby improving production capacity and efficiency.

In addition, in other implementations, a wheel disc is rotatably mounted at the proximal end surface of the housing 100. A first guide hole and a second guide hole are provided in the axial direction of the proximal end surface of the housing 100. The first guide hole and the second guide hole are located in the proximity of an outer ring wall of the wheel disc. An outer ring wall between the first guide hole and the second guide hole forms the first curved movement path. The first connecting portion 13 is abutted against an outer circumferential wall of the wheel disc. In this embodiment, it is not necessary to mount the annular groove 101 on the proximal end surface of the housing 100, but to directly mount the wheel disc on a rotating shaft on the proximal end surface of the housing 100. An outer circumferential wall surface of the wheel disc directly forms the movement path of the first connecting portion 13. On this basis, the wheel disc can be a rotating component, similar to the rotating disc in the above embodiment. When the first connecting portion 13 is forced to move along the outer circumferential wall surface of the wheel disc, the wheel disc rotates to reduce the friction. Additionally, the wheel disc can be fixed in a non-rotational manner. The first connecting portion 13 is provided with a rotating portion, which can be a roller. When the first connecting portion 13 is abutted against an outer circumference of the wheel disc and forced to move, the first connecting portion 13 is connected to the outer circumference of the wheel disc in a rolling manner through the roller.

In other embodiments, the proximal end surface of the housing 100 is provided with a first accommodating groove. The first connecting portion 13 is located in the first accommodating groove. The first accommodating groove is curved. Unlike the above embodiment, in this embodiment, the first accommodating groove, rather than the wheel disc or the rotating wheel 102 in the above embodiment, defines the movement path of the first connecting portion 13. The wheel disc or the rotating wheel 102 is usually cylindrical, so the movement path of the first connecting portion 13 is limited to a circular or fan-shaped surface. In this embodiment, the first accommodating groove is curved. It is not necessarily a regular circular arc, but can be a circular arc with different curvature radii or can be a curve.

Therefore, in order to solve the problem that there is a friction between a wall of the first accommodating groove and the first connecting portion 13 during the forced movement of the first connecting portion 13, the first connecting portion 13 is provided with a roller. The roller is abutted against a side wall of the first accommodating groove.

In an implementation of the present disclosure, the disposable section 10 of an endoscope handle further includes a second transmission assembly.

Figure 5:
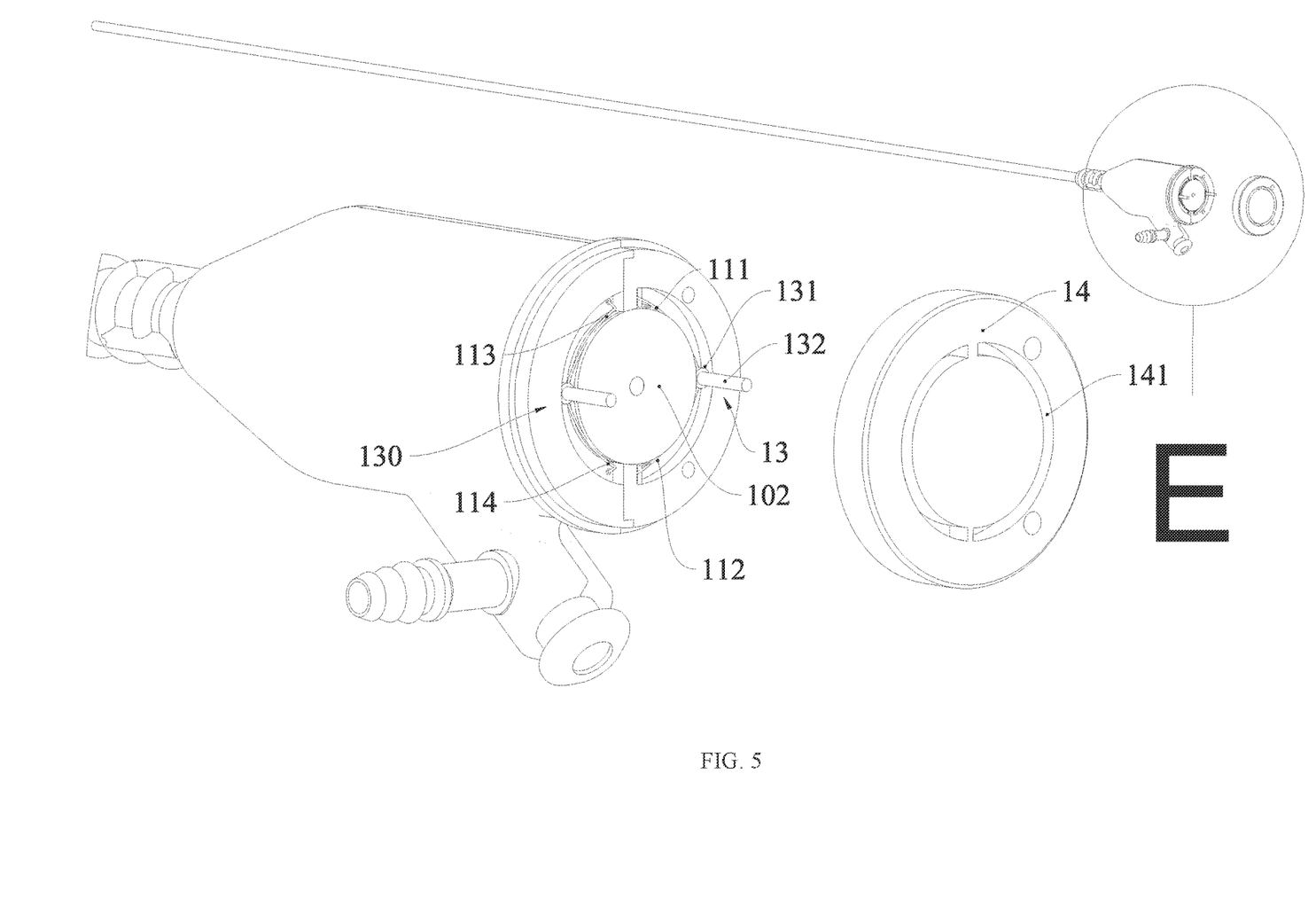
FIG. 5 is a structural diagram of a disposable section with two transmission assemblies according to an embodiment of the present disclosure.
Figure 6:
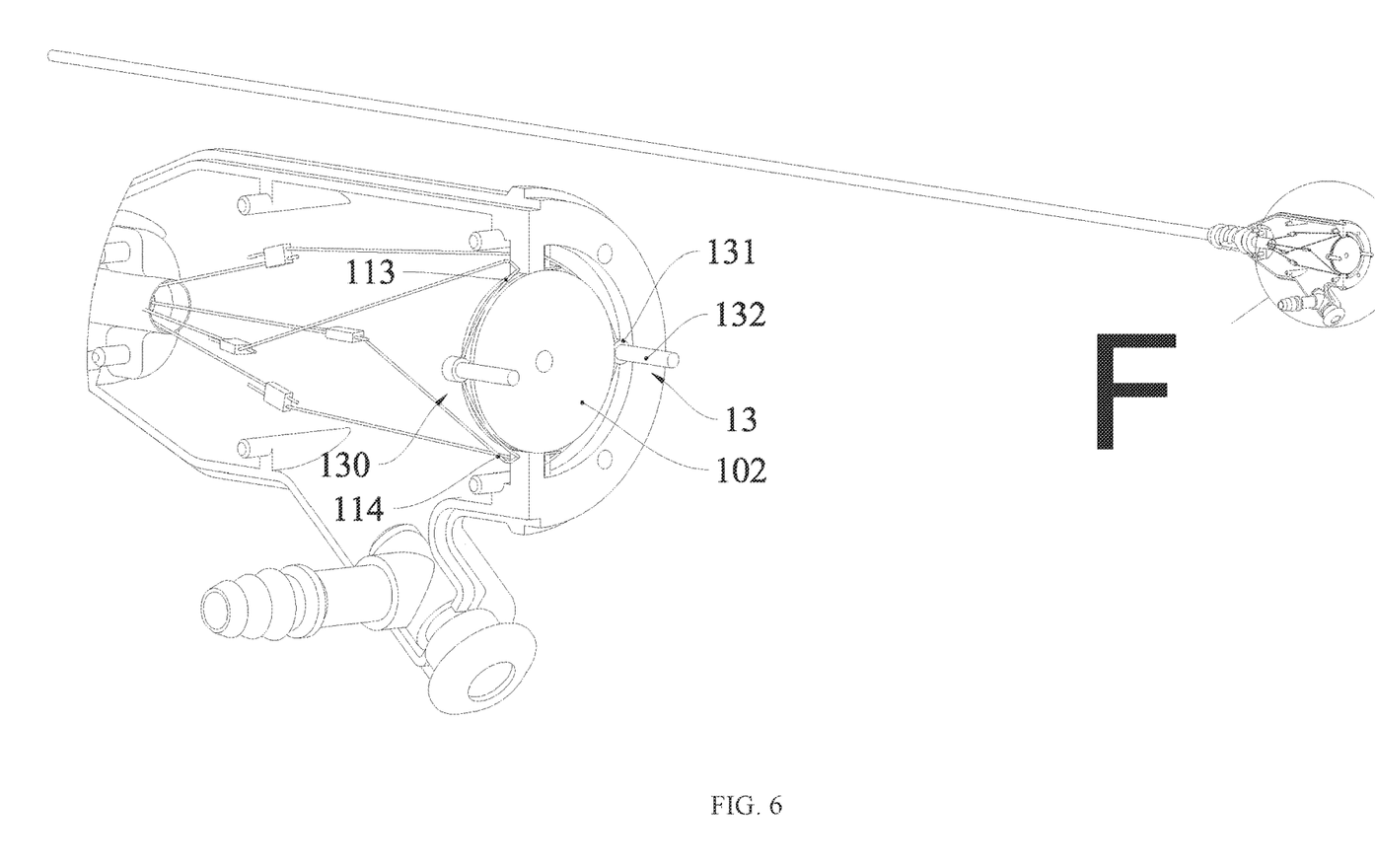
FIG. 6 is an internal view of the disposable section with two transmission assemblies according to the embodiment of the present disclosure.

The second transmission assembly includes: third traction wire 113, fourth traction wire 114, and second connecting portion 130. The third traction wire 113 and the fourth traction wire 114 are located in the inserting unit 11 of the endoscope. A distal end of the third traction wire 113 and a distal end of the fourth traction wire 114 are connected to the active bending section 12 at the distal end of the inserting unit 11. A proximal end of the third traction wire 113 and a proximal end of the fourth traction wire 114 are connected to the second connecting portion 130. The first transmission assembly is opposite to the second transmission assembly. The proximal end surface of the housing 100 is further provided with a second curved movement path. The second connecting portion 130 is located on the second curved movement path. The second curved movement path is curved. This implementation provides two transmission assemblies, namely the first transmission assembly and the second transmission assembly, and provides the first curved movement path and the second curved movement path. The first connecting portion 13 of the first transmission assembly and the second connecting portion 130 of the second transmission assembly independently move along the first curved movement path and the second curved movement path, providing more bending directions for the active bending section 12 than in above embodiment. The formation of the second curved movement path matches the formation of the first curved movement path in the above implementation.

An endoscope handle includes the above-mentioned disposable section 10 and reusable section 20. The disposable section 10 and the reusable section 20 are detachably connected.

A distal end of the reusable section 20 is provided with a matched portion that is configured to be connected to the first connecting portion 13. One of the first connecting portion 13 and the matched portion is a male connecting element, and the other of the first connecting portion 13 and the matched portion is a female connecting element. In the embodiments shown in FIGS. 2, 3, 5, and 6, the first connecting portion 13 is a male connecting element, including sliding portion 131 and connecting rod 132. The connecting rod 132 is connected to a matched portion located at the distal end of the reusable section 20. By driving a force application component of the reusable section 20, the matched portion drives the first connecting portion 13 to move along the first curved movement path and/or drives the second connecting portion 130 to move along the second curved movement path, causing the active bending section 12 to deflect in a preset direction.

The present disclosure further provides an endoscope, including the above-mentioned endoscope handle.

The above are merely preferred embodiments of the present disclosure, and not intended to limit the present disclosure. Any modifications, equivalent replacements, and improvements made within the spirit and principle of the present disclosure should fall within the protection scope of the present disclosure.

What is claimed is:

1. A disposable section of an endoscope handle, comprising:
 a housing, comprising a proximal end provided with a connecting portion, wherein the connecting portion is configured to be detachably connected to a reusable section of the endoscope handle;
 an inserting unit, wherein a proximal end of the inserting unit is mounted to a distal end of the housing; and
 a first transmission assembly, comprising: a first traction wire, a second traction wire, and a first connecting portion, wherein the first traction wire and the second traction wire are located in the inserting unit of an endoscope; and a distal end of the first traction wire and a distal end of the second traction wire are connected to an active bending section at a distal end of the inserting unit, and a proximal end of the first traction wire and a proximal end of the second traction wire are connected to the first connecting portion, wherein
 a proximal end surface of the housing forms a first curved movement path; the first curved movement path is orthogonal to an axial direction of the proximal end surface and located at a periphery of the proximal end surface of the housing; and the first connecting portion is movable along the first curved movement path.

2. The disposable section of the endoscope handle according to claim 1, wherein the proximal end surface of the housing is provided with an annular groove; a rotating wheel is rotatably mounted at a central area of the annular groove; a curved guide groove is formed between an outer edge of the rotating wheel and a ring wall of the annular groove; and the first connecting portion is slidably provided in the curved guide groove.

3. The disposable section of the endoscope handle according to claim 2, wherein an outer ring wall surface of the rotating wheel is provided with an accommodating groove.

4. An endoscope handle, comprising the disposable section of the endoscope handle according to claim 3 and the reusable section of the endoscope handle, wherein the disposable section and the reusable section are detachably connected; and
 a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

5. The disposable section of the endoscope handle according to claim 2, wherein two ends of the curved guide groove are respectively provided with a first through hole and a second through hole along the axial direction of the proximal end surface of the housing; and the first traction wire and the second traction wire are respectively threaded through the first through hole and the second through hole.

6. An endoscope handle, comprising the disposable section of the endoscope handle according to claim 5 and the reusable section of the endoscope handle, wherein the disposable section and the reusable section are detachably connected; and
 a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

7. An endoscope handle, comprising the disposable section of the endoscope handle according to claim 2 and the reusable section of the endoscope handle, wherein the disposable section and the reusable section are detachably connected; and a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

8. The disposable section of the endoscope handle according to claim 1, wherein a wheel disc is rotatably mounted at the proximal end surface of the housing; a first guide hole and a second guide hole are provided in the axial direction of the proximal end surface of the housing; the first guide hole and the second guide hole are located in a proximity of an outer ring wall of the wheel disc; an outer ring wall between the first guide hole and the second guide hole forms the first curved movement path; and the first connecting portion is abutted against an outer circumferential wall of the wheel disc.

9. An endoscope handle, comprising the disposable section of the endoscope handle according to claim 8 and the reusable section of the endoscope handle, wherein the disposable section and the reusable section are detachably connected; and a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

10. The disposable section of the endoscope handle according to claim 1, wherein the proximal end surface of the housing is provided with a first accommodating groove; the first connecting portion is located in the first accommodating groove; and the first accommodating groove is curved.

11. The disposable section of the endoscope handle according to claim 10, wherein the first connecting portion is provided with a roller, and the roller is abutted against a side wall of the first accommodating groove.

12. An endoscope handle, comprising the disposable section of the endoscope handle according to claim 11 and the reusable section of the endoscope handle, wherein the disposable section and the reusable section are detachably connected; and a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

13. An endoscope handle, comprising the disposable section of the endoscope handle according to claim 10 and the reusable section of the endoscope handle, wherein the disposable section and the reusable section are detachably connected; and a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

14. The disposable section of the endoscope handle according to claim 1, further comprising:

a second transmission assembly, comprising: a third traction wire, a fourth traction wire, and a second connecting portion, wherein the third traction wire and the fourth traction wire are located in the inserting unit of the endoscope; and a distal end of the third traction wire and a distal end of the fourth traction wire are connected to the active bending section at the distal end of the inserting unit, and a proximal end of the third traction wire and a proximal end of the fourth traction wire are connected to the second connecting portion;

the first transmission assembly is opposite to the second transmission assembly; and the proximal end surface of the housing is further provided with a second curved movement path; the second connecting portion is located on the second curved movement path; and the second curved movement path is curved.

15. An endoscope handle, comprising the disposable section of the endoscope handle according to claim 14 and the reusable section of the endoscope handle, wherein the disposable section and the reusable section are detachably connected; and a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

16. An endoscope handle, comprising the disposable section of the endoscope handle according to claim 1 and the reusable section of the endoscope handle, wherein the disposable section and the reusable section are detachably connected; and a distal end of the reusable section is provided with a matched portion, the matched portion is configured to be connected to the first connecting portion; and a first one of the first connecting portion and the matched portion is a male connecting element, and a second one of the first connecting portion and the matched portion is a female connecting element.

17. An endoscope, comprising the endoscope handle according to claim 16.

* * * * *